US005270950A

United States Patent [19]

Cowley et al.

[11] Patent Number: 5,270,950

[45] Date of Patent: Dec. 14, 1993

[54] APPARATUS AND A METHOD FOR LOCATING A SOURCE OF ACOUSTIC EMISSION IN A MATERIAL

[75] Inventors: Peter H. Cowley, Quarndon; Simon D. King, Wilmorton; Neil Randall, Matlock, all of England

[73] Assignee: Rolls-Royce and Associates Limited, Derby, England

[21] Appl. No.: 760,909

[22] Filed: Sep. 17, 1991

[51] Int. Cl.[5] ...................... G01H 11/08; G01H 17/00

[52] U.S. Cl. .............................. 364/551.01; 364/507; 364/508; 73/587; 367/127

[58] Field of Search .................. 367/127, 907; 73/587, 73/801, 12.04, 588, 598; 364/507, 508, 551.01

[56] References Cited

U.S. PATENT DOCUMENTS

| | | | |
|---|---|---|---|
| 3,875,381 | 4/1975 | Wingfield et al. | 367/127 |
| 3,919,883 | 11/1975 | Nakamura et al. | 73/587 |
| 4,009,463 | 2/1977 | Vercellotti et al. | 367/127 |
| 4,353,255 | 10/1982 | Fukuda et al. | 73/587 |
| 4,417,478 | 11/1983 | Min-Chung-Jon et al. | 73/801 |
| 4,459,851 | 7/1984 | Crostack | 73/587 |
| 4,592,034 | 5/1986 | Sachse et al. | 367/127 |
| 4,641,526 | 2/1987 | Izumi et al. | 367/127 |
| 4,979,124 | 12/1990 | Sachse et al. | 364/507 |
| 5,010,503 | 4/1991 | Patron et al. | 364/569 |

FOREIGN PATENT DOCUMENTS

| | | |
|---|---|---|
| 0207527 | 7/1987 | European Pat. Off. . |
| 0317322 | 5/1989 | European Pat. Off. . |
| 1343694 | 1/1974 | United Kingdom . |

OTHER PUBLICATIONS

The Journal of the Acoustical Society of America, vol. 85, No. 3, Mar. 1989, pp. 1226–1235.

Proceedings of the Society of Photo-Optical Instrumentation Engineers SPIE vol. 1294, 1990, pp. 545–556, and Application of Artificial Neural Networks Conference Apr. 18–20, 1990 (-non written Disclosure).

*Primary Examiner*—Jack B. Harvey

*Assistant Examiner*—Jae H. Cho

*Attorney, Agent, or Firm*—Cushman, Darby & Cushman

[57] ABSTRACT

An apparatus for locating a source of acoustic emission in a material comprises four spaced transducers coupled to the material. Each transducer produces an output signal corresponding to a detected acoustic emission activity, and each output signal is amplified, rectified and enveloped before being supplied to a processor. Artificially induced acoustic emission events, of known location, are generated in the material. The processor measures the times taken for each output signal corresponding to artificially induced acoustic emission events, to exceed two predetermined amplitudes from a datum time. A neural network analyzes the measured times to exceed the predetermined amplitudes for the output signals corresponding to the artificially induced acoustic emission events and infers the mathematical relationship between values of time and location of acoustic emission event. The times taken for each output signal, corresponding to acoustic emission events of unknown source location, to exceed two predetermined amplitudes from the datum are measured and are used to calculate the location of the unknown source with the mathematical relationship deduced by the neural network.

18 Claims, 2 Drawing Sheets

APPARATUS AND A METHOD FOR LOCATING A SOURCE OF ACOUSTIC EMISSION IN A MATERIAL

FIELD OF THE INVENTION

The present invention relates to an apparatus and a method for locating a source of acoustic emissions in a material.

Acoustic emissions, or stress waves, arise in a material due to impacts of loose components on the material, from a sudden movement of a defect, such as a crack, in the material or a sudden movement of an unbond between two joined components forming the material.

DESCRIPTION OF THE PRIOR ART

Previously sources of acoustic emission have been located by measuring the time of arrival of an acoustic emission pulse at each of several transducers. The differences in the times of arrival of the acoustic emission pulse at each of. the transducers is calculated and triangulation techniques are used to deduce the location of the source of the acoustic emission.

This technique has several disadvantages. Firstly the times of arrival of the acoustic emission pulse at each of the transducers has to be measured accurately, the error in the deduced position of the acoustic emission source is determined by the combination of the uncertainties in the velocity of sound in the particular material and the uncertainty in the timing of the arrival of the acoustic emission pulse at each of the transducers. Secondly the geometry and composition of the material have to be such that the relative velocity of sound in every direction may be calculated. In composite materials, or other materials with complex structure, for example sheets of metal separated by a metal honeycomb, the appropriate calculations of the velocity may be very time consuming or may be impossible. Thirdly the accuracy of the calculated position is affected by attenuation of the acoustic emission pulse due to absorption, or scattering, of energy as the acoustic emission pulse passes through the material between the source and the transducers. The acoustic emission pulse becomes spread out in time, and the time of arrival of the acoustic emission pulse is overestimated.

SUMMARY OF THE INVENTION

The present invention seeks to provide an apparatus for locating a source of acoustic emission in a material in which the above mentioned problems are overcome.

Accordingly the present invention provides an apparatus for locating a source of acoustic emissions in a material comprising at least three spaced transducers acoustically coupled to the material, each transducer being arranged to detect acoustic emissions in the material and being arranged to produce a corresponding electrical output signal, measuring means to measure the time taken for each of the electrical output signals to equal or exceed at least two predetermined amplitudes from a datum time, means for analyzing the values of time taken for each of the electrical output signals to equal or exceed each of the at least two predetermined amplitudes for a plurality of artificially induced acoustic emission events having known locations to infer the mathematical relationship between the values of time for each of the electrical output signals and the location of a source of acoustic emission, means for storing the deduced mathematical relationship, means for calculating from the values of time taken for each of the electrical output signals to equal or exceed each of the at least two predetermined amplitudes for an acoustic emission of unknown source location and the stored mathematical relationship the location of the source of the acoustic emission.

Preferably there are four spaced apart transducers.

Preferably the analysing means is a neural network.

Preferably the measuring means measures the time taken for each of the electrical output signals to equal or exceed up to five predetermined amplitudes from the datum time.

The measuring means may measure the time taken for each electrical output signal to reach the maximum amplitude.

The measuring means may measure the maximum amplitude of each of the electrical output signals or may measure the cumulative amplitude of each electrical output signal over a predetermined time period, the analyzing means also analyses the maximum amplitudes or cumulative amplitudes for the plurality of artificially induced acoustic emission events to infer the mathematical relationship, and the calculating means locates the source of the acoustic emission of unknown source location from the maximum amplitude or cumulative amplitude of each electrical output signal from the acoustic emission of unknown source location.

The datum time may be the time at which the electrical output signal of one of the transducers equals or exceeds a first predetermined threshold.

The present invention also provides an apparatus for locating the source of an acoustic emission in a material comprising at least three transducers acoustically coupled to the material, each transducer being arranged to detect acoustic emissions in the material and being arranged to produce a corresponding electrical output signal, measuring means to measure the rate of increase of amplitude for each of the electrical output signals, means for analyzing the rate of increase of amplitude for each of the electrical output signals for a plurality of artificially induced acoustic emission events having known locations to infer the mathematical relationship between the rates of increase of amplitude for each of the electrical output signals and the location of a source of acoustic emission, means for storing the deduced mathematical relationship, means for calculating from the rates of increase of amplitude for each of the electrical output signals for an acoustic emission of unknown source location and the stored mathematical relationship the location of the source of the acoustic emission.

Preferably there are four spaced apart transducers.

Preferably the analysing means is a neural network.

The present invention also provides a method of locating a source of acoustic emission in a material comprising detecting a plurality of artificially induced acoustic emission events having known source locations at at least three spaced transducers acoustically coupled to the material, measuring the time taken for the acoustic emission activity detected by each transducer to equal or exceed at least two predetermined amplitudes from a datum time for each of the artificially induced acoustic emission events, inferring the mathematical relationship between the values of time taken for the acoustic emission activity detected by each transducer to equal or exceed each of the at least two predetermined amplitudes for each of the artificially induced acoustic emission events having known source locations and the location of an acoustic emission event, storing the mathematical relationship, detecting a subsequent acoustic emission event having an unknown source location at the at least three spaced transducers, measuring the time taken for the subsequent acoustic emission activity detected by each transducer to equal or exceed the at least two predetermined amplitudes from a datum time for the acoustic emission event having an unknown source location, calculating from the values of time taken for the subsequent acoustic emission activity detected by each transducer to equal or exceed each of the at least two predetermined amplitudes for the acoustic emission event having an unknown source location and the stored mathematical relationship the location of the subsequent acoustic emission event.

Preferably a neural network infers the mathematical relationship.

Preferably there are four spaced transducers.

BRIEF DESCRIPTION OF THE DRAWINGS

The present invention will be more fully described by way of example, with reference to the accompanying drawings, in which.

DETAILED DESCRIPTION OF THE INVENTION

Figure 1:
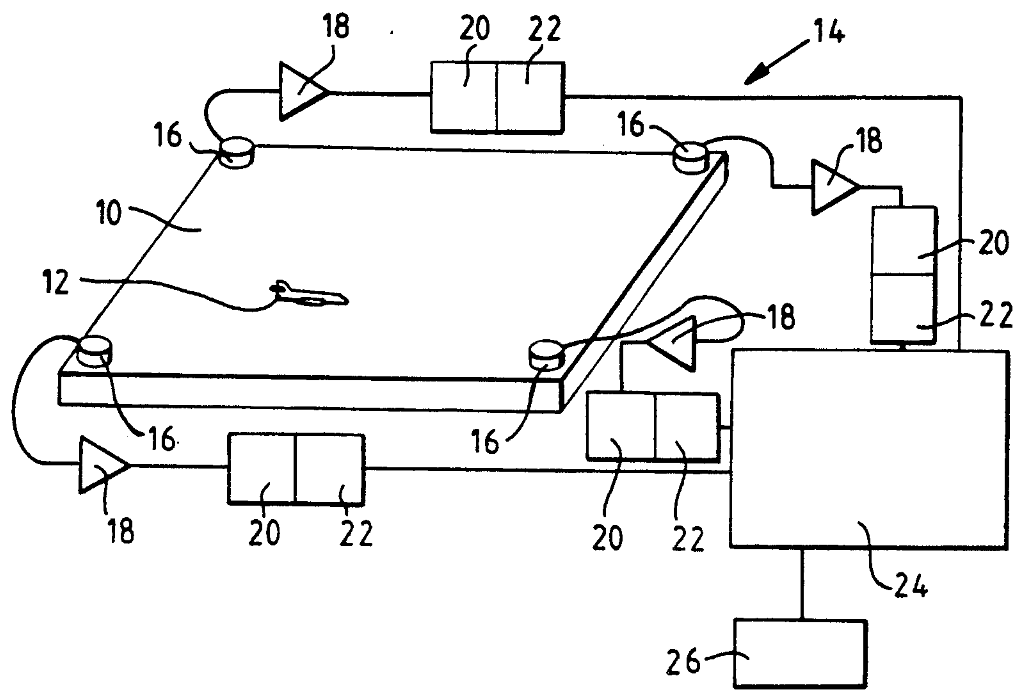
FIG. 1 is an apparatus for locating a source of acoustic emission in a material according to the present invention.

An apparatus 14 for locating a source 12 of acoustic emission in a material 10, shown in FIG. 1, comprises four spaced apart transducers 16 acoustically coupled to the material 10. Each transducer 16 is arranged to detect acoustic emissions, or stress waves, generated in the material 10 as a result of an impact, by frictional processes or produced by sudden movement of a defect such as a crack or an unbond between two joined components forming the material. Each transducer 16 is arranged to produce an electrical output signal dependent upon the acoustic emission activity detected. The transducers 16 are commonly piezoceramic elements, although other suitable types of transducer may be used.

The electrical output signal produced by each transducer 16 is supplied to a respective amplifier 18. Each amplifier 18 amplifies the respective electrical output signal and each amplifier 18 may incorporate filters to select the required frequency band or frequency bands. Each amplified electrical output signal is rectified by a rectifier 20 and is then supplied to a signal enveloper 22 which envelopes the rectified electrical output signal. As an example the enveloper 22 envelopes the rectified electrical output signal with a 100 micro second time constant, although other suitable time constants may be used.

Each rectified electrical output signal is supplied to a processor 24. The processor 24 processes the rectified electrical output signals to locate the source of an acoustic emission 12 and displays the result on a display 26. The processor 24 comprises a plurality of threshold crossing detection devices 28, a plurality of timing devices 30 and a plurality of peak amplitude detecting devices 32. The threshold crossing detection devices detect when the amplitude of the rectified electrical output signal from each transducer 16 equals or exceeds at least two different predetermined amplitudes. The timing devices detect the times at which each rectified electrical output signal equals or exceeds the predetermined amplitudes relative to a datum time and also detects the time at which each rectified electrical output signal reaches its maximum amplitude relative to the datum time. The peak amplitude detection devices measure the maximum amplitude reached by each of the rectified electrical output signals. The processor 24 also comprises an analyzing device, for example a neural network for or a software implementation of a neural network 34 for analysing the times at which each of the rectified electrical output signals equals or exceeds the at least two predetermined amplitudes and the times at which each of the rectified electrical output signals reaches its maximum amplitude and also for analysing the maximum amplitude of each of the rectified electrical output signals.

A neural network 34 is a pattern recognition and classification technique which has been described in many publications, for example "An artificial Neural Network Tutorial—Part 1—Basics" by K. N. Karna and D. M. Breen published in "The International Journal of Neural Networks" volume 1 number 1, January 1989.

The neural network is trained by generating a number of artificially induced acoustic emission events, at a number of different known locations in the material 10. The artificially induced acoustic emission events are produced for example by breaking a pencil lead against the material 10, although other suitable methods of artificially inducing acoustic emission events into the material 10 may be used. The locations of these artificially induced acoustic emission events are known and these are used as the desired outputs of the neural network for training purposes. The relative times at which each of the rectified electrical output signals equals or exceeds the at least two predetermined amplitudes, together with the relative times at which each of the rectified electrical output signals reaches its maximum amplitude and the values of the maximum amplitude for each of the rectified electrical output signals for the artificially induced acoustic emission events are used as the inputs to the neural network for training purposes. The neural network infers, or deduces, the mathematical relationship between the inputs, the relative times taken to equal or exceed each of the predetermined amplitudes and the maximum amplitudes, and the values of the maximum amplitudes for each of the rectified electrical output signals, and the desired outputs, the locations of the artificially induced acoustic emission events.

The processor 24 also has a store 36 in which the mathematical relationship, correlation or knowledge, inferred by the neural network is stored in the form of a key matrix of values, known as the input signal weights.

Once the neural network has been trained, and the mathematical relationship is held in the store of the processor 24, the relative times at which each of the rectified electrical output signals equals or exceeds the at least two predetermined amplitudes, together with the relative times at which each of the rectified electrical output signals reaches its maximum amplitude and the values of the maximum amplitude for each of the rectified electrical output signals, for an acoustic emission event of unknown source location, are used with the stored mathematical relationship to calculate the location of the acoustic emission source 12. The result of the calculation is shown on the display 26.

The differences in time between any two of the predetermined amplitudes for each of the rectified electrical output signals is a measure of the rate of increase of amplitude for the rectified electrical output signals. The neural network is effectively working out the rate of increase of amplitude for each of the rectified electrical output signals and then working out the mathematical relationship between the rates of increase of amplitude and the location of an acoustic emission.

Figure 2:
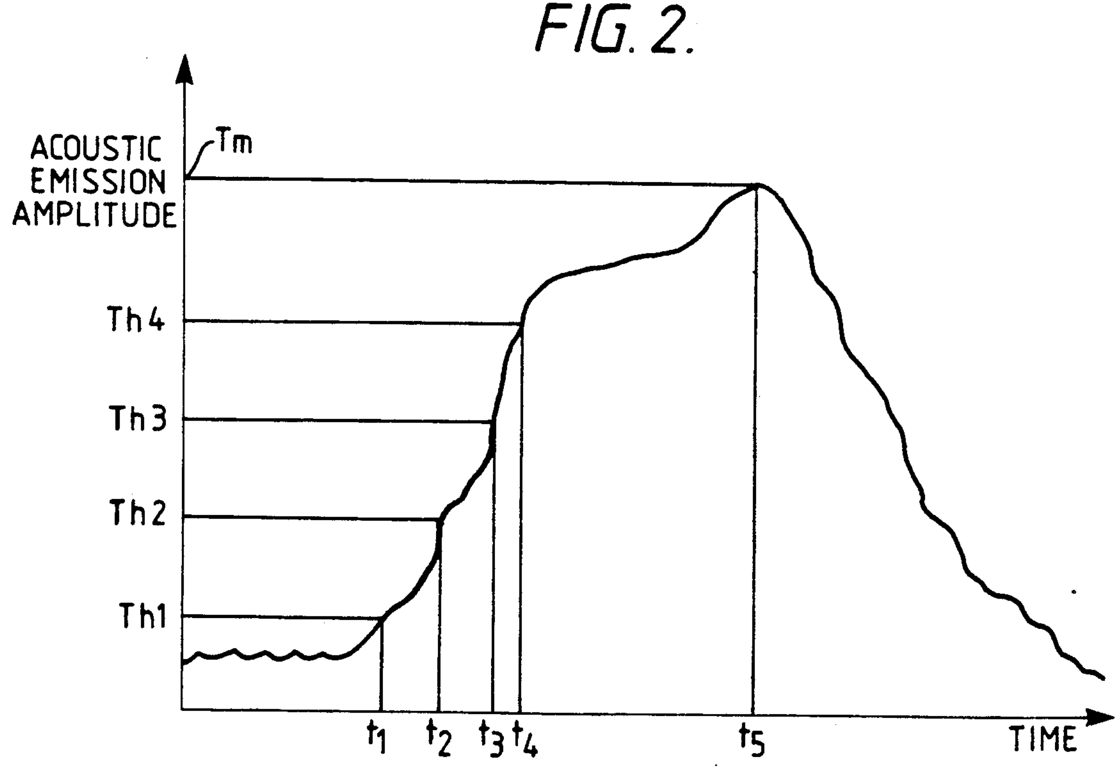
FIG. 2 is a graph of acoustic emission amplitude versus time for one of the transducers used in the apparatus shown in FIG. 1.
Figure 3:
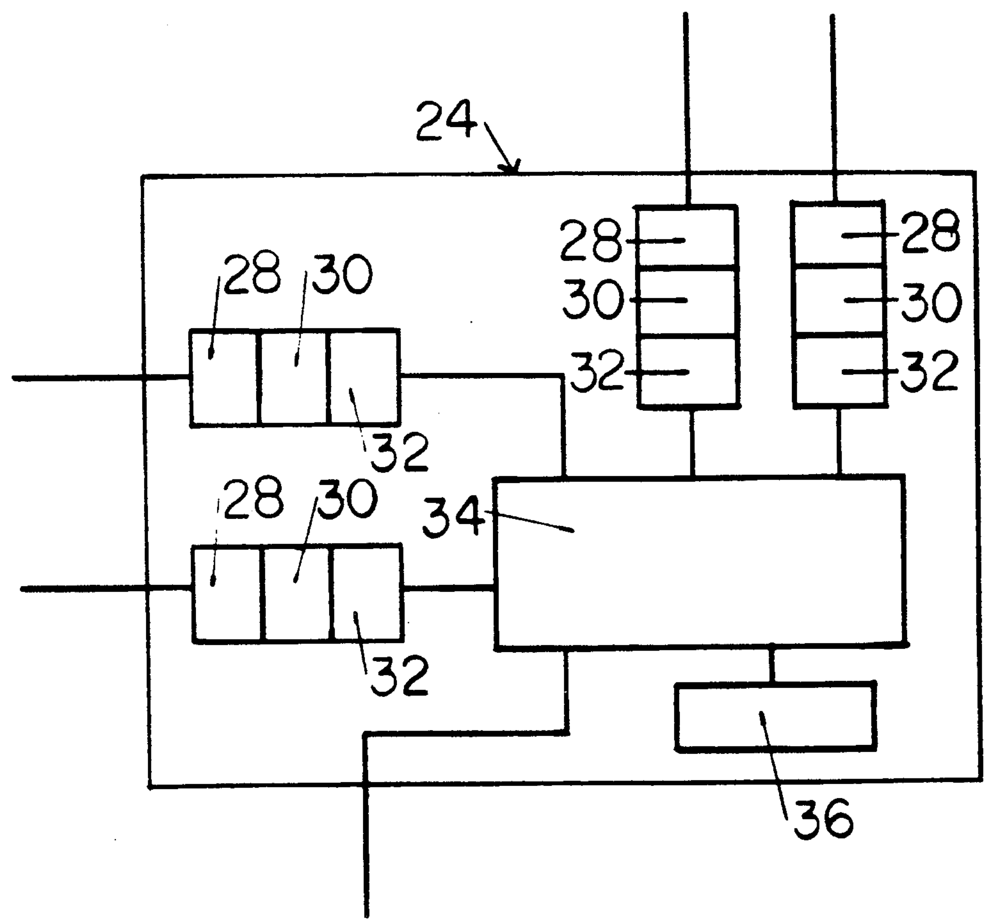
FIG. 3 is a schematic illustration of the components of the processor used in the present invention.

In FIG. 2 is shown a representative graph of acoustic emission amplitude versus time for an acoustic emission pulse received by one of the transducers 16 shown in FIG. 1. The graph shows the predetermined amplitudes $Th_1$, $Th_2$, $Th_3$ and $Th_4$ detected by the threshold crossing detection devices and the corresponding times $t_1$, $t_2$, $t_3$ and $t_4$ at which the acoustic emission amplitude equals the predetermined amplitudes. The graph also shows the maximum amplitude $T_m$ and the corresponding time $t_5$ at which the acoustic emission amplitude reaches the maximum amplitude.

Thus in the above example, discussed with reference to FIG. 1, the threshold crossing devices detect when the amplitude of each rectified electrical output signal reached the predetermined amplitudes $Th_1$, $Th_2$, $Th_3$ and $Th_4$ and the peak amplitude detecting devices detects when the amplitude of each rectified electrical output signal reaches the maximum amplitude $T_m$. The timing devices detect the corresponding times $t_1$, $t_2$, $t_3$, $t_4$ and $t_5$ at which each rectified electrical output signal equals the predetermined amplitudes $Th_1$, $Th_2$, $Th_3$, $Th_4$ and the maximum amplitude $T_m$.

Thus for each artificially induced acoustic emission event there are 24 numerical values inputted to the neural network for the training process, and for an acoustic emission of unknown source location there are 24 numerical values inputted to calculate the source location with the stored mathematical relationship.

The datum time is any suitable time from which the relative times of all the other events are calculated. The datum time may for example be the time $t_1$ at which one of the rectified electrical output signals equals or exceeds the first predetermined amplitude $Th_1$.

Although the description has referred to the use of four transducers to locate the source of an acoustic emission any number of transducers equal to or greater than three may be used.

The description has referred to detecting the times at which four predetermined amplitudes and the maximum amplitude are reached for each rectified electrical output signal, together with a measure of the maximum amplitudes, this gives an accurate location of an acoustic emission source. It may be possible to measure the cumulative amplitude of each rectified electrical output signal over a fixed time period at predefined time intervals as an alternative to measuring the maximum amplitudes.

If the accuracy of location of the acoustic emission source is not as critical, the maximum amplitudes and the times to reach the maximum amplitudes may not need to be measured, thus only sixteen numerical values are enputted to the neural network for each artificially induced acoustic emission event, and only sixteen numerical values are used to calculate the source of an acoustic emission event having an unknown source location, for four transducers.

The relative times for each of the rectified electrical output signals to exceed two predetermined amplitudes together with the neural network technique for calculating the location of the acoustic emission source is more accurate, is less prone to extraneous noise and requires less accurate measurement of the acoustic emission pulse than the use of times of arrival of the acoustic emission pulse at the transducers combined with triangulation techniques used in the prior art.

We claim:

1. An apparatus for locating a source of acoustic emissions in a material comprising:

at least three spaced transducers acoustically coupled to the material, each transducer being arranged to detect acoustic emissions in the material and being arranged to produce a corresponding electrical output signal, measuring means to measure the time taken for each of the electrical output signals to equal or exceed at least two predetermined amplitudes from a datum time, means for analyzing the values of time taken for each of the electrical output signals to equal or exceed each of the at least two predetermined amplitudes for a plurality of artificially induced acoustic emission events having known locations to infer a mathematical relationship between the values of time for each of the electrical output signals and the location of a source of acoustic emission, means for storing the deduced mathematical relationship, means for calculating from the values of time taken for each of the electrical output signals to equal or exceed each of the at least two predetermined amplitudes for an acoustic emission of unknown source location and the stored mathematical relationship the location of the source of the acoustic emission.

2. An apparatus as claimed in claim 1 in which there are four spaced apart transducers.

3. An apparatus as claimed in claim 1 in which the analysing means is a neural network.

4. An apparatus as claimed in claim 1 in which the measuring means measures the time taken for each of the electrical output signals to equal or exceed up to five predetermined amplitudes from the datum time.

5. An apparatus as claimed in claim 1 in which the measuring means measures the time taken for each electrical output signal to reach a maximum amplitude.

6. An apparatus as claimed in claim 1 in which the measuring means measures the maximum amplitude of each of the electrical output signals the analyzing means also analyzes the maximum amplitudes for the plurality of artificially induced acoustic emission events, to infer the mathematical relationship, and the calculating means locates the source of the acoustic emission of unknown source location from the maximum amplitude of each electrical output signal from the acoustic emission of unknown source location.

7. An apparatus as claimed in claim 1 in which the datum time is the time at which the electrical output signal of one of the transducers equals or exceeds a first predetermined threshold.

8. An apparatus for locating the source of an acoustic emission in a material comprising:

at least three transducers acoustically coupled to the material, each transducer being arranged to detect acoustic emissions in the material and being arranged to produce a corresponding electrical output signal, measuring means to measure the rate of increase of amplitude for each of the electrical output signals, means for analysing the rate of increase of amplitude for each of the electrical output signals for a plurality of artificially induced acoustic emission events having known locations to infer a mathematical relationship between the rates of increase of amplitude for each of the electrical output signals and the location of a source of acoustic emission, means for storing the deduced mathematical relationship, means for calculating from the rates of increase of amplitude for each of the electrical output signals for an acoustic emission of unknown source location and the stored mathematical relationship the location of the source of the acoustic emission.

9. An apparatus as claimed in claim 8 in which there are four spaced apart transducers.

10. An apparatus as claimed in claim 8 in which the analysing means is a neural network.

11. An apparatus as claimed in claim 8 in which the measuring means measures the maximum amplitude of each of the electrical output signals the analyzing means also analyzes the maximum amplitudes for the plurality of artificially induced acoustic emission events to infer the mathematical relationship, and the calculating means locates the source of the acoustic emission of unknown source location from the maximum amplitude of each electrical output signal from the acoustic emission of unknown source location.

12. A method of locating a source of acoustic emission in a material comprising detecting a plurality of artificially induced acoustic emission events having known source locations at at least three spaced transducers acoustically coupled to the material, measuring the time taken for the acoustic emission activity detected by each transducer to equal or exceed at least two predetermined amplitudes from a datum time for each of the artificially induced acoustic emission events, inferring a mathematical relationship between the values of time taken for the acoustic emission activity detected by each transducer to equal or exceed each of the at least two predetermined amplitudes for each of the artificially induced acoustic emission events having known source locations and the location of an acoustic emission event, storing the mathematical relationship, detecting a subsequent acoustic emission event having an unknown source location at the at least three spaced transducers, measuring the time taken for the subsequent acoustic emission activity detected by each transducer to equal or exceed the at least two predetermined amplitudes from a datum time for the acoustic emission event having an unknown source location, calculating from the values of time taken for the subsequent acoustic emission activity detected by each transducer to equal or exceed each of the at least two predetermined amplitudes for the acoustic emission event having an unknown source location and the stored mathematical relationship the location of the subsequent acoustic emission event.

13. A method as claimed in claim 12 in which a neural network infers the mathematical relationship.

14. A method as claimed in claim 12 in which there are four spaced transducers.

15. A method as claimed in claim 12 in which the time taken for each of the electrical output signals to equal or exceed up to five predetermined amplitudes from the datum time is measured.

16. A method as claimed in claim 12 in which the time taken for each electrical output signal to reach the maximum amplitude is measured.

17. An apparatus as claimed in claim 1, in which the measuring means measures the cumulative amplitude of each electrical output signal over a predetermined time period, the analyzing means also analyzes the cumulative amplitudes for the plurality of artificially induced acoustic emission events, to infer the mathematical relationship, and the calculating means locates the source of the acoustic emission of unknown source location from the cumulative amplitude of each electrical output signal from the acoustic emission of unknown source location.

18. An apparatus as claimed in claim 8, in which the measuring means measures the cumulative amplitude of each of the electrical output signals over a predetermined time period, the analyzing means also analyzes cumulative amplitudes for the plurality of artificially induced acoustic emission vents to infer the mathematical relationship, and the calculating means locates the source of the acoustic emission of unknown source location from the cumulative amplitude of each electrical output signal from the acoustic emission of unknown source location.

* * * * *